(12) United States Patent
Garza et al.

(10) Patent No.: US 12,290,458 B2
(45) Date of Patent: *May 6, 2025

(54) STENTS HAVING A HYBRID PATTERN AND METHODS OF MANUFACTURE

(71) Applicant: Vactronix Scientific, LLC, San Antonio, TX (US)

(72) Inventors: Armando Garza, San Jose, CA (US); Julio C. Palmaz, Napa, CA (US); Michael Poor, San Jose, CA (US)

(73) Assignee: Vactronix Scientific, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,624

(22) Filed: Jul. 17, 2023

(65) Prior Publication Data

US 2024/0016630 A1 Jan. 18, 2024

Related U.S. Application Data

(60) Continuation of application No. 16/595,877, filed on Oct. 8, 2019, now Pat. No. 11,701,246, which is a
(Continued)

(51) Int. Cl.
*B23K 26/36* (2014.01)
*A61F 2/91* (2013.01)
(Continued)

(52) U.S. Cl.
CPC .............. *A61F 2/915* (2013.01); *A61F 2/91* (2013.01); *A61L 31/022* (2013.01); *B21D 51/16* (2013.01);
(Continued)

(58) Field of Classification Search
None
See application file for complete search history.

(56) References Cited

U.S. PATENT DOCUMENTS 4,733,665 A 3/1988 Palmaz
5,102,417 A 4/1992 Palmaz
(Continued)

FOREIGN PATENT DOCUMENTS

WO 1999023977 5/1999
WO 2010124286 10/2010
WO 2013134560 9/2013

OTHER PUBLICATIONS

Notification of Transmittal of the International Search Report and the Written Opinion of the International Searching Authority, or the Declaration. Foreign Application No. PCT/US2013/070098. Dated Mar. 21, 2014.
(Continued)

*Primary Examiner* — Shamim Ahmed
(74) *Attorney, Agent, or Firm* — Rosenbaum IP, P.C.; David G. Rosenbaum

(57) ABSTRACT

An intravascular stent and method of making an intervascular stent having a hybrid pattern a. The hybrid pattern comprises a plurality of circumferentially self-expansible members comprising a plurality of interconnected, geometrically deformable closed cells, adjacent self-expansible members interconnected by a plurality of bridge members linking a first interconnection between two closed cells in a first self-expansible member to a second interconnection between two closed cells in a second self-expansible member, wherein the second interconnection is circumferentially offset and non-adjacent to the first interconnection.

23 Claims, 8 Drawing Sheets

Related U.S. Application Data continuation-in-part of application No. 15/432,087, filed on Feb. 14, 2017, now Pat. No. 10,433,989, which is a division of application No. 13/678,335, filed on Nov. 15, 2012, now Pat. No. 9,566,633.

(51) Int. Cl.

| | | |
|---|---|---|
| *A61F 2/915* | (2013.01) | |
| *A61L 31/02* | (2006.01) | |
| *B21D 51/16* | (2006.01) | |
| *B23K 26/362* | (2014.01) | |
| *C03C 14/00* | (2006.01) | |
| *C23C 14/00* | (2006.01) | |
| *C23C 14/04* | (2006.01) | |
| *C23C 14/58* | (2006.01) | |
| *C30B 33/10* | (2006.01) | |
| *A61L 31/08* | (2006.01) | |
| *B23K 101/06* | (2006.01) | |

(52) U.S. Cl.
CPC ............ *B23K 26/36* (2013.01); *B23K 26/362* (2013.01); *C23C 14/0005* (2013.01); *C23C 14/04* (2013.01); *C23C 14/5873* (2013.01); *C30B 33/10* (2013.01); *A61F 2210/0076* (2013.01); *A61F 2230/0054* (2013.01); *A61F 2240/001* (2013.01); *A61L 31/028* (2013.01); *A61L 31/088* (2013.01); *A61L 2420/02* (2013.01); *B23K 2101/06* (2018.08)

(56) References Cited

U.S. PATENT DOCUMENTS

| | | | |
|---|---|---|---|
| 5,195,984 A | 3/1993 | Schatz | |
| 5,879,381 A | 3/1999 | Moriuchi et al. | |
| 5,895,407 A | 4/1999 | Jayaraman | |
| 6,432,132 B1 | 8/2002 | Cottone et al. | |
| 6,598,276 B2 | 7/2003 | Pinchasik et al. | |
| 7,556,644 B2 | 7/2009 | Burpee et al. | |
| 7,691,461 B1 | 4/2010 | Prabhu | |
| 7,803,180 B2 | 9/2010 | Burpee et al. | |
| 7,988,723 B2 | 8/2011 | Beach et al. | |
| 10,433,989 B2 | 10/2019 | Garza et al. | |
| 2002/0156525 A1 | 10/2002 | Smith et al. | |
| 2003/0114921 A1 | 6/2003 | Yoon | |
| 2004/0127972 A1 | 7/2004 | Kitaoka et al. | |
| 2004/0172804 A1 | 9/2004 | Hopkins | |
| 2004/0186551 A1 | 9/2004 | Kao et al. | |
| 2005/0216076 A1 | 9/2005 | Kveen et al. | |
| 2007/0129786 A1 | 6/2007 | Beach et al. | |
| 2007/0185564 A1 | 8/2007 | Pacetti et al. | |
| 2007/0208416 A1 | 9/2007 | Burpee et al. | |
| 2008/0051875 A1 | 2/2008 | Cottone et al. | |
| 2008/0097571 A1 | 4/2008 | Denison et al. | |
| 2009/0036964 A1 | 2/2009 | Heringes et al. | |
| 2009/0036976 A1 | 2/2009 | Beach et al. | |
| 2009/0088831 A1 | 4/2009 | Goto | |
| 2009/0240319 A1 | 9/2009 | Craven | |
| 2010/0094394 A1 | 4/2010 | Beach et al. | |
| 2010/0121430 A1 | 5/2010 | Kveen et al. | |
| 2010/0286760 A1 | 11/2010 | Beach et al. | |
| 2011/0029064 A1 | 2/2011 | Burpee et al. | |
| 2011/0210108 A1 | 9/2011 | Bialas et al. | |
| 2011/0245910 A1 | 10/2011 | Beach et al. | |
| 2012/0073733 A1* | 3/2012 | Ngo ......................... | A61F 2/89 156/196 |
| 2013/0268055 A1 | 10/2013 | Cottone et al. | |

OTHER PUBLICATIONS

Written Opinion of the International Searching Authority. Foreign Application No. PCT/US2013/070098. Dated Mar. 21, 2014.
International Preliminary Report on Patentability. Foreign Application No. PCT/US2013/070098. Dated May 28, 2015.
European Search Report. Foreign Application No. PCT/US2013/070098. Dated Sep. 21, 2016.
Office Action issued in corresponding foreign application. Canadian Application No. 2,891,624. Foreign Application No. PCT/US2013/070098. Dated: Sep. 25, 2019.

* cited by examiner

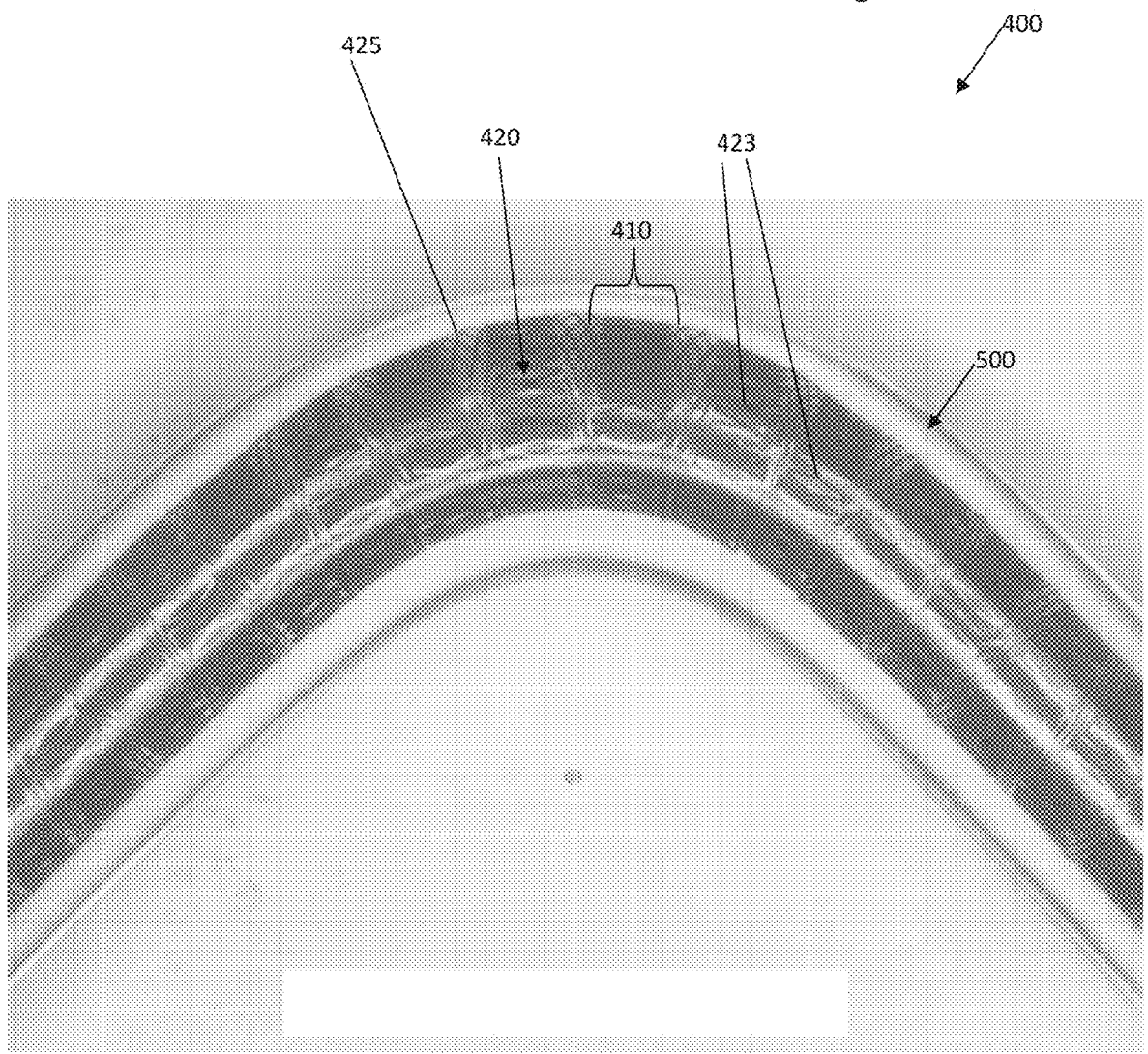

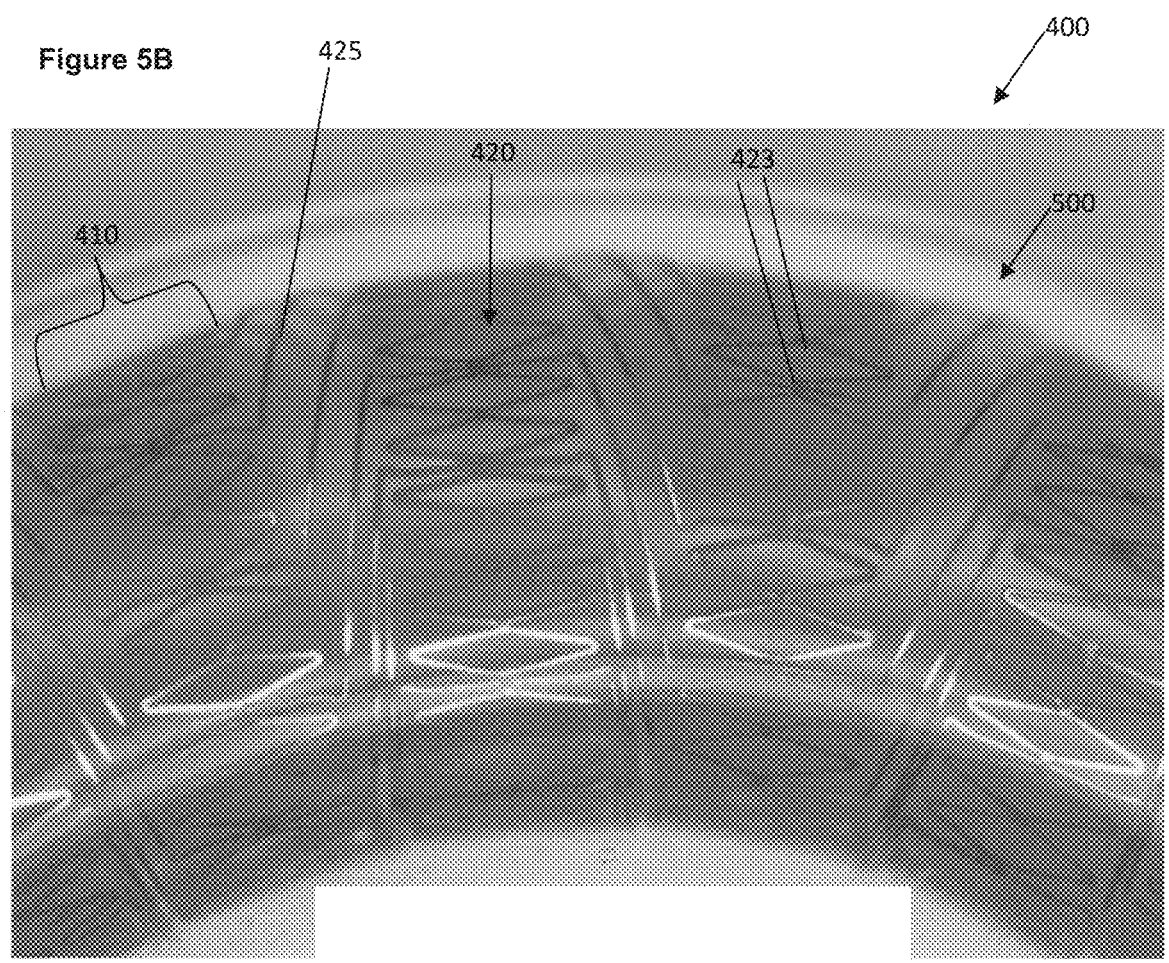

STENTS HAVING A HYBRID PATTERN AND METHODS OF MANUFACTURE

CROSS-REFERENCE TO RELATED APPLICATIONS

This application is a continuation of, commonly owned U.S. patent application Ser. No. 16/595,877, filed Oct. 8, 2019, to issue as U.S. Pat. No. 11,701,246 on Jul. 18, 2023; which is a continuation application of U.S. patent application Ser. No. 15/432,087, filed Feb. 14, 2017, now U.S. Pat. No. 10,433,989; which is a divisional U.S. patent application Ser. No. 13/678,335, filed Nov. 15, 2012, now U.S. Pat. No. 9,566,633,

BACKGROUND

The invention relates to intravascular stents and methods for manufacturing intravascular stents. In particular, the intravascular stent have a hybrid pattern and may be formed from an elongated ribbon having portions etched and cut therefrom.

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Prior art stents have some functional limitations due to their current design. For example, the prior art stent can collapse when it is bent around a sharp angle. What is needed is an improved stent that is more flexible and can be implanted in tightly bent vessels.

The method of manufacturing hybrid pattern intravascular stents from thin ribbons of material provides advantages over known methods by reducing the cost of base materials (as compared to tubular materials), improves consistency and verification of wall thicknesses, and provides improved access to the surfaces that comprise the inner diameter of a stent, for imparting grooves or other patterns thereupon, prior to forming the stent.

SUMMARY OF THE INVENTION

Disclosed in one embodiment of the present invention is an implantable medical device, such as but not limited to an intravascular stent, comprising: a plurality of circumferentially self-expansible members comprising a plurality of geometrically deformable closed cells, the closed cells being interconnected to form a tubular structure; and a plurality of bridge members interconnecting adjacent circumferentially self-expansible members, each bridge member linking a first interconnection between two adjacent closed cells in a first circumferentially self-expansible member to a second interconnection between two adjacent closed cells in a second circumferentially self-expansible member. In some embodiments, the second interconnection is circumferentially offset and non-adjacent to the first interconnection. The hybrid pattern is a combination of closed and open cells, which serves to provide adequate scaffold strength (from the closed cells) with flexibility (from the open cells). In some embodiments, the geometrically deformable closed cells have a generally diamond expanded shape. In other embodiments, the geometrically deformable closed cells may take other expanded shapes, including but not limited to circles, ovals, triangles, rectangles, squares, and/or the like.

In some embodiments, the plurality of circumferentially self-expansible members have a wall thickness of less than 75 micrometers. In some embodiments, the plurality of circumferentially self-expansible members have a wall thickness of between 40 microns and 50 microns.

In some embodiments, the bridge members are capable of expansion outward from the circumferential plane to serve as a distributed flare for device fixation to prevent migration.

In some embodiments, the device comprises a biocompatible material. Materials to make the inventive devices are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In some embodiments, the pattern of closed cells and bridge members provides flow diversion properties.

In some embodiments, the orientation of the plurality of bridge members alternates between adjacent pairs of circumferentially self-expansible members.

In some embodiments, the device is crimpable to an outer diameter of less than 1 mm.

In some embodiments, the device has an expanded diameter of between 3 mm and 5 mm.

In some embodiments, the device is capable of bending without severe buckling on an inner surface proximate the position of the bend.

Each of the preferred embodiments of the present invention is preferably fabricated by employing a vapor deposition technique which entails vapor depositing a stent-forming metal onto a substrate. The substrate may be planar or cylindrical and is either pre-patterned with one of the preferred geometries of first and interconnecting members, in either positive or negative image, or the substrate may be un-patterned. Where the substrate is un-patterned, the deposited stent-forming metal is subjected to post-deposition patterning to pattern the deposited stent-forming metal into one of the preferred geometries of the first and interconnecting members. In all embodiments of the present invention fabricated by vapor deposition techniques, the need for post-deposition processing of the patterned endoluminal stent, e.g., modifying the surface of the stent by mechanical, electrical, thermal, or chemical machining or polishing, is eliminated or minimized.

In one embodiment, disclosed is a method of manufacturing an intravascular stent, comprising the steps of: providing a thin ribbon of material having a predetermined thickness and width; winding the thin ribbon around a mandrel; and shaping the wound thin ribbon into a desired stent frame shape.

In some embodiments, the predetermined thickness and width is obtained by passing the thin ribbon of material through at least one of a wire flattener and a width trimmer.

In some embodiments, the method further comprises the step of patterning at least one surface of the thin ribbon, prior to or simultaneous with the step of winding around the mandrel. In some embodiments, the patterning comprises laser patterning to impart at least one feature on the at least one surface of the thin ribbon. In some embodiments, the pattern is a series of grooves on at least one surface of the thin ribbon, preferably the surface that will comprise the inner diameter of the finished stent. In other embodiments, the pattern may be a plurality of microgrooves imparted onto the luminal and/or abluminal surface of the stent, as is more fully described in International Publication No. WO 99/23977, published 20 May 1999, which is commonly assigned with the present application and is hereby incorporated by reference. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

In some embodiments, the material is a nickel-titanium alloy. In some embodiments, materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In some embodiments, the method further comprises the step of polishing the thin ribbon, prior to or simultaneous with the step of winding around the mandrel.

In some embodiments, the mandrel is generally cylindrical in shape. In some embodiments, the stent frame is generally cylindrical in shape.

In some embodiments, the method further comprises the step of laser cutting a stent strut pattern into the thin ribbon, prior to or simultaneous with the step of winding around the mandrel. In some embodiments, the laser cutting is a cold process that produces minimal slag.

It is further contemplated that the stent method uses a thin wire or ribbon of material, such metals like NiTi or other materials, and wind the wire or ribbon on a mandrel to create a stent frame. Prior to, or while winding, the ribbon surfaces are easily accessible from all sides, hence one side, possibly what will become the internal dimension of the stent, of the ribbon could be patterned with a tool such as a laser creating a grooved surface. This wound tube with a patterned internal dimension, would then be further processed, as necessary, like other stents disclosed in the prior art.

In particular, a flat ribbon or wire comprised of biocompatible material is provided wherein the ribbon has predetermined length, width and thickness. In some embodiments, the ribbon or wire may be passed through a wire flattener and/or a width trimmer to achieve the desired thickness and/or width. A stent is formed from this material by forming cuts in the material so that the cut material can be stretched to form an undulating wave-like pattern. The cut ribbon is then spirally wound into a generally cylindrical shape to form a stent segment. Plural stent segments can be affixed to one another in longitudinal succession to form an elongate stent using a connector which is formed from the ribbon. Interconnection between adjacent stent segments is achieved by combining two connectors where the connectors may be fabricated at one-half their original width and bonded together by welding or other means.

In particular, one skilled in the art commences with a spool or ribbon or wire with a predetermined thickness and width. In some embodiments, the ribbon or wire may be passed through a wire flattener and/or a width trimmer to achieve the desired thickness and/or width. In some embodiments, a pattern is imparted on the interior dimension surface of the ribbon. The pattern may be imparted by utilizing a laser to pattern the interior dimension surface. Next, a cut pattern for stent struts is imparted onto the ribbon. In some embodiments, a laser may be used to create the cut pattern for stent struts. In some embodiments, an optional surface polish is placed on the interior dimension surface. Finally, the wire or ribbon is wound on a mandrel altering and shaping the wire or ribbon in a predetermined shape/pattern, thus creating an expandable stent, or other medical device.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 5A is a low magnification image showing a high-density pattern micro-stent in a glass tube through a 90-degree bend; FIG. 5B is a high magnification image showing a high density pattern micro-stent in a glass tube through a 90 degree bend.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The present invention is an improved stent which has good radial strength to hold a vessel open and improved flexibility that is suitable for implantation in more sharply bent vessels.

In accordance with the invention, the foregoing advantages have been achieved through the herein disclosed hybrid pattern intravascular stents and methods of manufacturing hybrid pattern intravascular stents utilizing thin ribbons of material having portions cut and etched therefrom to form hybrid patterns.

Figure 1:
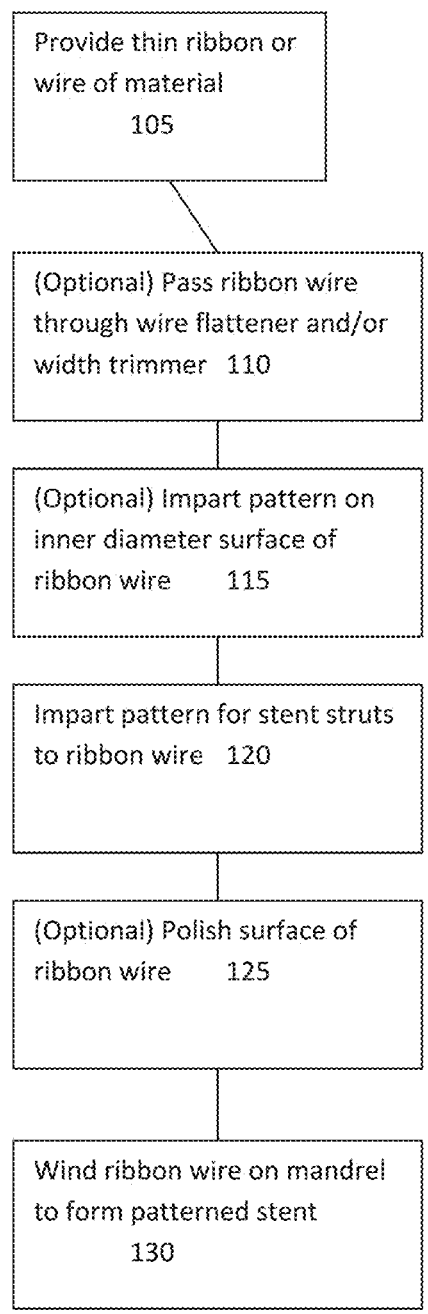
FIG. 1 is a combined logic flow and block diagram illustrating a method of manufacturing a hybrid pattern stent using ribbon wire.

In one embodiment, depicted in FIG. 1 as a combined logic flow and block diagram, disclosed is a method (100) of manufacturing an intravascular stent, comprising the steps of: providing a thin ribbon or wire of material (105) having a predetermined thickness and width; winding the thin ribbon around a mandrel (130); and shaping the wound thin ribbon into a desired stent frame shape.

In some embodiments, the material is a nickel-titanium alloy. In some embodiments, materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In some embodiments, the predetermined thickness and width is obtained by passing the thin ribbon of material through at least one of a wire flattener and a width trimmer (110).

In some embodiments, the method (100) further comprises the step of patterning at least one surface of the thin ribbon (115), prior to or simultaneous with the step of winding around the mandrel (130). In some embodiments, the patterning (115) comprises laser patterning to impart at least one feature on the at least one surface of the thin ribbon. In some embodiments, the pattern is a series of grooves on at least one surface of the thin ribbon, preferably the surface that will comprise the inner diameter of the finished stent. In other embodiments, the pattern may be a plurality of microgrooves imparted onto the luminal and/or abluminal surface of the thin ribbon, as is more fully described in International Publication No. WO 99/023977, published 20 May 1999, which is commonly assigned with the present application and is hereby incorporated by reference in its entirety.

In some embodiments, the method (100) further comprises the step of laser cutting a stent strut pattern into the thin ribbon (120), prior to or simultaneous with the step of winding around the mandrel (130). In some embodiments, the laser cutting (120) is a cold process that produces minimal slag.

In some embodiments, the method (100) further comprises the step of polishing the thin ribbon (125), prior to or simultaneous with the step of winding around the mandrel (130).

In some embodiments, the mandrel is generally cylindrical in shape. In some embodiments, the formed stent frame is generally cylindrical in shape.

It is further contemplated that the stent method uses a thin wire or ribbon of material, such metals like NiTi or other materials, and wind the wire or ribbon on a mandrel to create a stent frame. Prior to, or while winding, the ribbon surfaces are easily accessible from all sides, hence one side, possibly what will become the internal dimension of the stent, of the ribbon could be patterned with a tool such as a laser creating a grooved surface. This wound tube with a patterned internal dimension, would then be further processed, as necessary, like other stents disclosed in the prior art.

In particular, a flat ribbon or wire comprised of biocompatible material is provided wherein the ribbon has predetermined length, width and thickness. In some embodiments, the ribbon or wire may be passed through a wire flattener and/or a width trimmer to achieve the desired thickness and/or width. A stent is formed from this material by forming cuts in the material so that the cut material can be stretched to form an undulating wave-like pattern. The cut ribbon is then spirally wound into a generally cylindrical shape to form a stent segment. Plural stent segments can be affixed to one another in longitudinal succession to form an elongate stent using a connector which is formed from the ribbon. Interconnection between adjacent stent segments is achieved by combining two connectors where the connectors may be fabricated at one-half their original width and bonded together by welding or other means.

In particular, one skilled in the art commences with a spool or ribbon or wire with a predetermined thickness and width. In some embodiments, the ribbon or wire may be passed through a wire flattener and/or a width trimmer to achieve the desired thickness and/or width. In some embodiments, a pattern is imparted on the interior dimension surface of the ribbon. The pattern may be imparted by utilizing a laser to pattern the interior dimension surface. Next, a cut pattern for stent struts is imparted onto the ribbon. In some embodiments, a laser may be used to create the cut pattern for stent struts. In some embodiments, an optional surface polish is placed on the interior dimension surface. Finally, the wire or ribbon is wound on a mandrel altering and shaping the wire or ribbon in a predetermined shape/pattern, thus creating an expandable stent, or other medical device. In specific instances, particularly for Nitinol, it may make sense to "train" parts to expand to final diameters via shape setting using heat treatment(s)/annealing. This additional processing will likely be followed by descale/oxide removal chemical treatments and electropolishing to achieve final surface finish desired.

Figure 2:
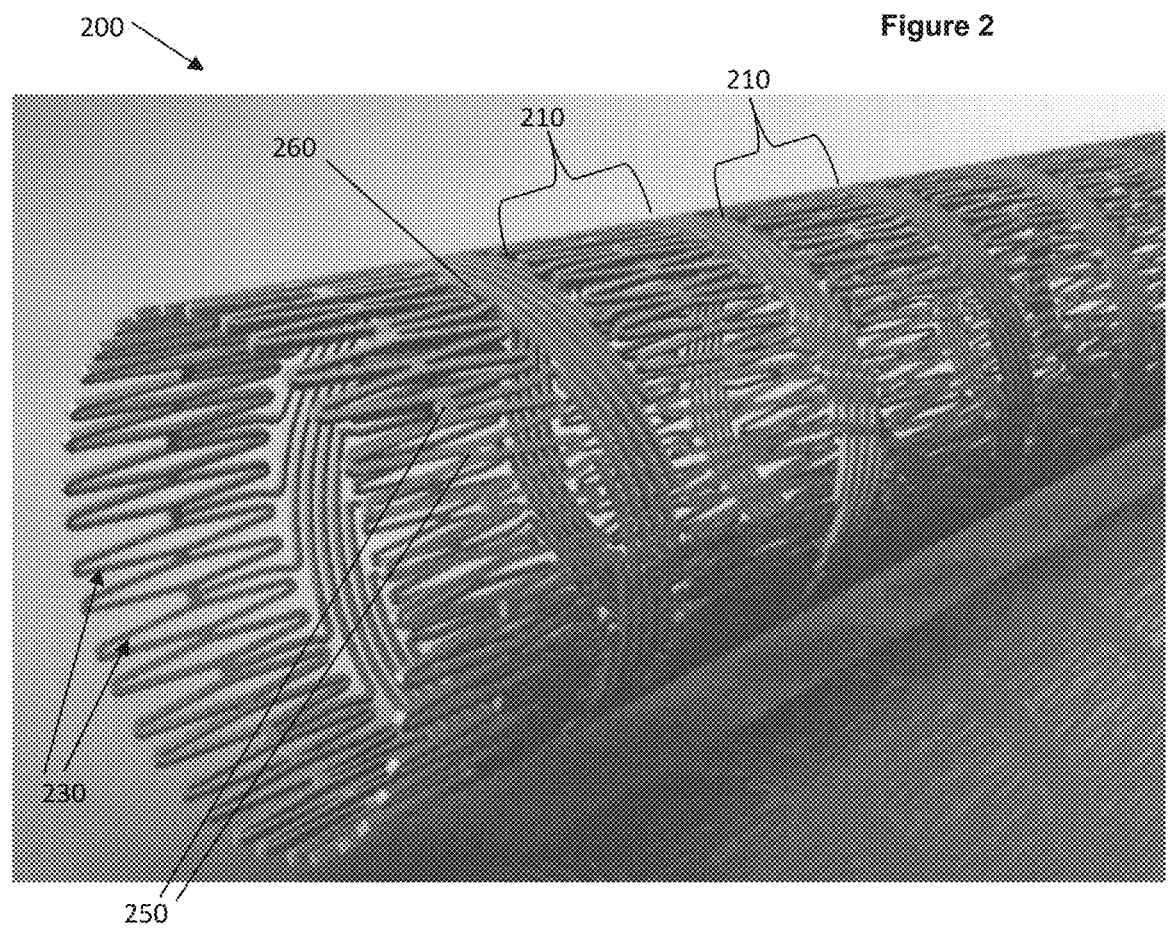
FIG. 2 is an isometric view of a hybrid pattern micro-stent.
Figure 3:
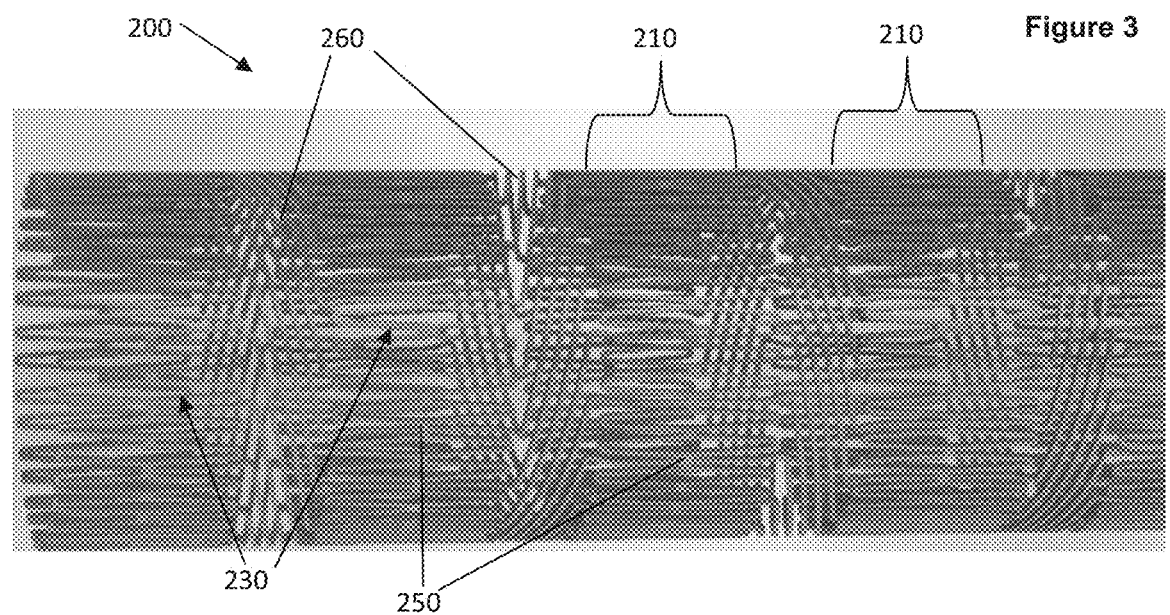
FIG. 3 is a side view of a hybrid pattern micro-stent.

FIG. 2 depicts an isometric view of an implantable medical device 200, such as but not limited to an intravascular stent, comprising: a plurality of circumferentially self-expansible members 210, each comprising a plurality of geometrically deformable closed cells 230, the closed cells 230 being interconnected at interconnections 250 to form a tubular structure; and a plurality of bridge members 260 interconnecting adjacent circumferentially self-expansible members 210, each bridge member 260 linking a first interconnection 250 between two adjacent closed cells 230 in a first circumferentially self-expansible member 210 to a second interconnection 250 between two adjacent closed cells 230 in a second circumferentially self-expansible member 210. In many embodiments, the second interconnection 250 is circumferentially offset and non-adjacent to the first interconnection 250. In some embodiments, the geometrically deformable closed cells 230 have a generally diamond expanded shape. FIG. 3 depicts a side view of the implantable medical device 200 of FIG. 2. In other embodiments, the geometrically deformable closed cells 230 may take other expanded shapes, including but not limited to circles, ovals, triangles, rectangles, squares, and/or the like.

In some embodiments, the hybrid stent pattern may allow for improved stent actuation using a start tube comprised of laminated layers of nitinol, stainless steel, L-605, MP35N, PtCr, TiTa, or other stent making materials. In some embodiments, it may be feasible to use (although after galvanic coupling evaluations) dissimilar metals to "enhance" the mechanical performance with respect to strength, toughness and possibly shape memory effect if Nitinol is involved. Using the metals listed in conjunction with Nitinol may possibly enhance the radiopacity of the resulting device and improve chemical/visual. In some embodiments, the stent may further comprise a layer of radiopaque material.

In some embodiments, the plurality of circumferentially self-expansible members 210 each have a wall thickness of less than 75 micrometers. In some embodiments, the plurality of circumferentially self-expansible members 210 each have a wall thickness of between 40 microns and 50 microns. Alternatively, the thickness of the members 210 may be between 1 micron and 1000 microns depending on the strength and thickness desired. Generally, the thin wall nature of the hybrid pattern stent 200 serves to discourage thrombogenicity and allows for low delivery profile.

Preferably, the hybrid pattern is a combination of closed cells 230 and open cells or bridges 260, which serves to simultaneously provide adequate scaffold strength (from the closed cells 230) and flexibility (from the open cells or bridges 260). In addition, long bridge lengths can allow for extreme and efficient propagation of stent longitudinal length in bends without significantly sacrificing longitudinal compliance. This may further allow high flexibility through torturous anatomy, as demonstrated in FIGS. 5A-B and 8. In some embodiments, the bridge interconnect interval or length may be altered to enhance or lessen longitudinal flexibility, as desired for a particular application of a given hybrid pattern stent. Bridge members may to enhance or lessen the longitudinal flexibility. In additional embodiments, varying the strut width or the shape (diversions from straight elements) of the bridge interconnect may adjust stiffness.

In some embodiments, the device 200 comprises a biocompatible material. Materials to make the inventive devices are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Alternatively, other biocompatible pseudo-metals and polymers may be used.

In some embodiments, the pattern of closed cells 230 and bridge members 260 provides flow diversion properties.

In some embodiments, the orientation of the plurality of bridge members 260 alternates between adjacent pairs of circumferentially self-expansible members 210, thereby allowing for a smooth and uniform crimp and/or expansion mechanism. In some embodiments, the orientation of the plurality of bridge members 260 is the same between adjacent pairs of circumferentially self-expansible members 210.

In some embodiments, the device 200 is crimpable to an outer diameter of less than 1 mm. In some embodiments, the device 200 has an expanded diameter of between 3 mm and 5 mm. In some embodiments, the device 200 is capable of bending without severe buckling on an inner surface proximate the position of the bend (see FIGS. 5A and 8).

Figure 4:
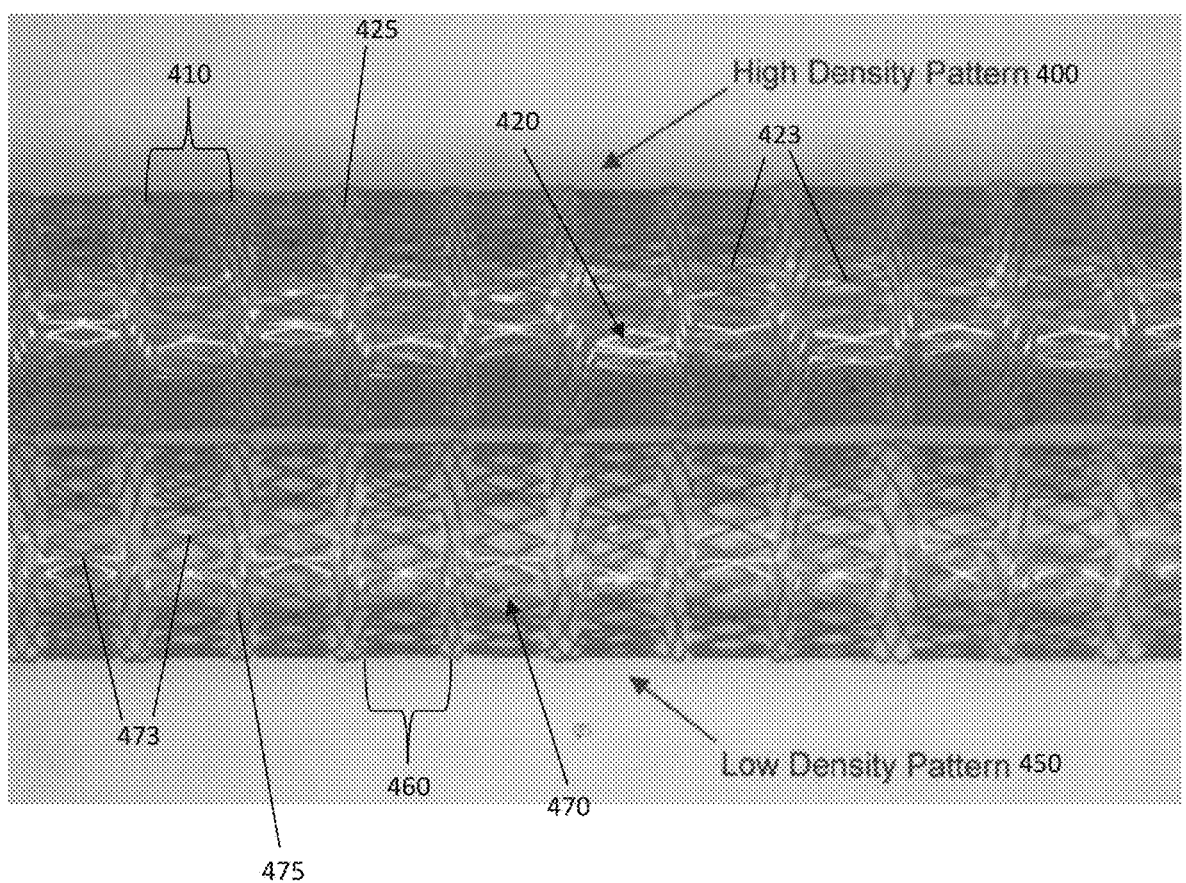
FIG. 4 is a low magnification image showing high density (top) and low density (bottom) hybrid pattern micro-stents.
Figure 6:
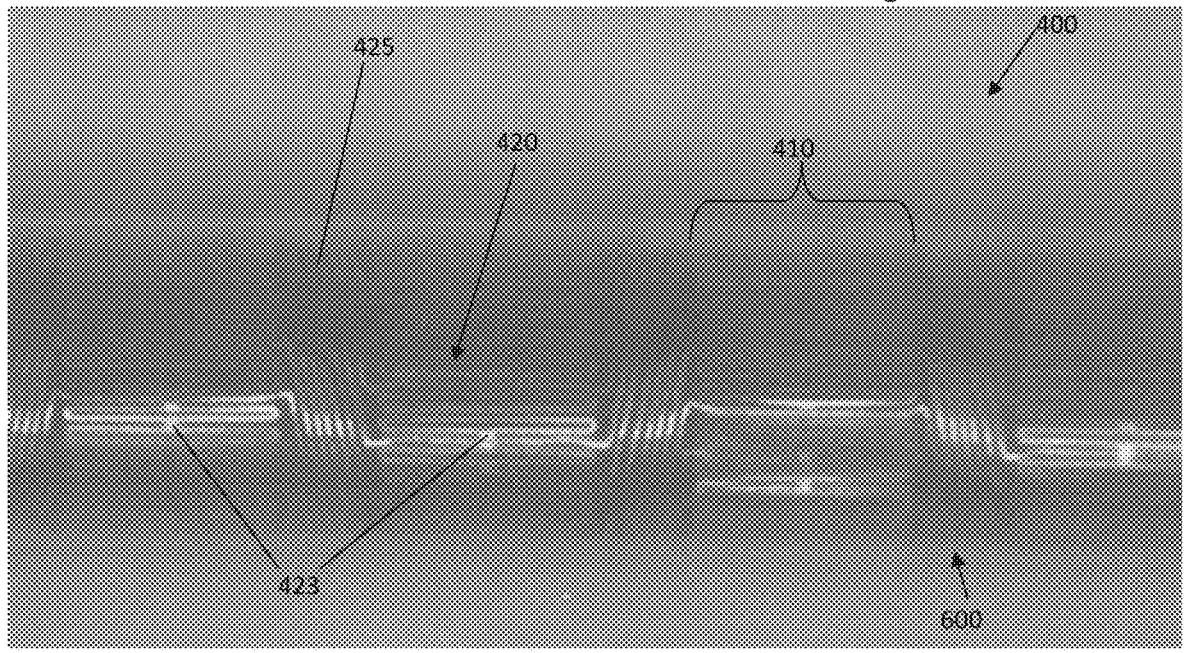
FIG. 6 is a high-density micro-stent crimped configuration constrained by a PTFE tube.

In some embodiments, as shown in FIGS. 4-6, a dense hybrid pattern 400 may serve to constrain plaque, especially vulnerable plaque.

FIG. 4 depicts two distinct hybrid pattern embodiments of the present invention—a high density hybrid pattern stent 400 and a low-density hybrid pattern stent 450. Both patterns have a plurality of circumferentially self-expansible members 410, 460, each comprising a plurality of geometrically deformable closed cells 420, 470, the closed cells 420, 470 being interconnected at interconnections 423, 473 to form a tubular structure; and a plurality of bridge members 425, 475 interconnecting adjacent circumferentially self-expansible members 410, 460, each bridge member 425, 475 linking a first interconnection 423, 473 between two adjacent closed cells 420, 470 in a first circumferentially self-expansible member 410, 460 to a second interconnection 423, 473 between two adjacent closed cells 420, 470 in a second circumferentially self-expansible member 410, 460, wherein the second interconnection 423, 473 is circumferentially offset and non-adjacent to the first interconnection 423, 473.

FIG. 5A illustrates a high-density pattern stent 400 in a glass tube 500 having a 3 mm inner diameter, through a 90-degree bend. FIG. 5B is an enlarged view of a portion of the high density pattern stent 400 of FIG. 5A.

FIG. 6 illustrates is a high-density pattern stent 400 in a crimped configuration constrained by a PTFE tube 600. In some embodiments, in the crimped configuration, the high-density pattern stent 400 has an outer diameter between about 1 mm and about 1.5 mm.

Figure 7:
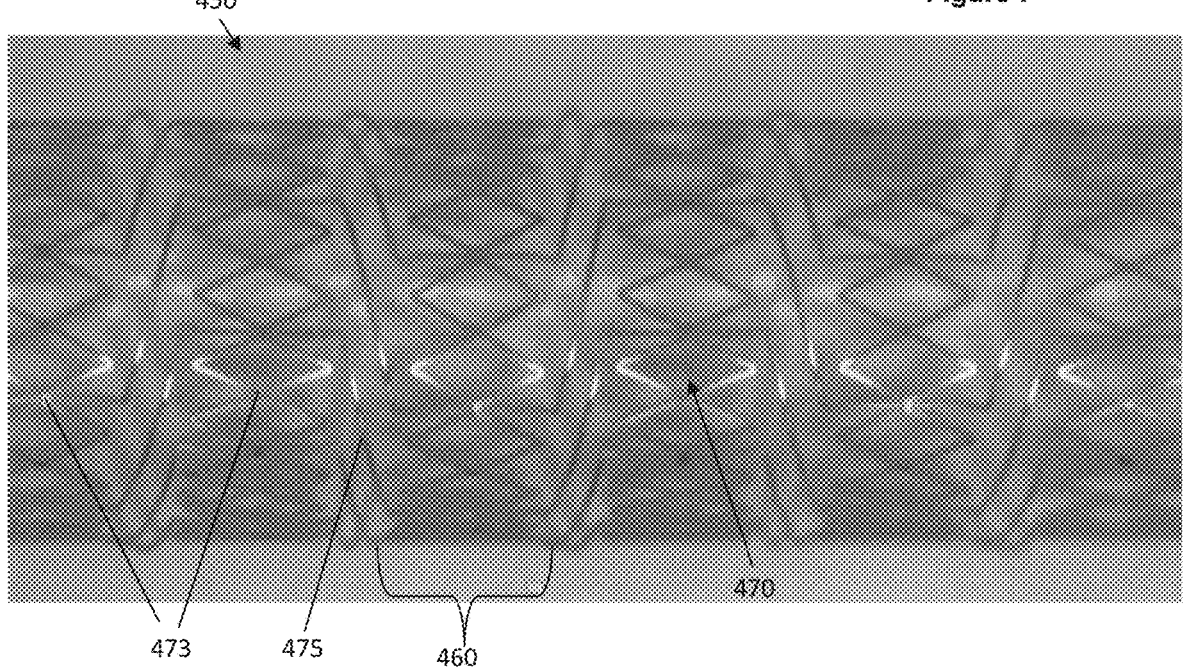
FIG. 7 is a low magnification image of a low-density micro-stent.

FIG. 7 illustrates a low-density pattern stent 450 having an outer diameter of about 3.5 mm.

Figure 8:
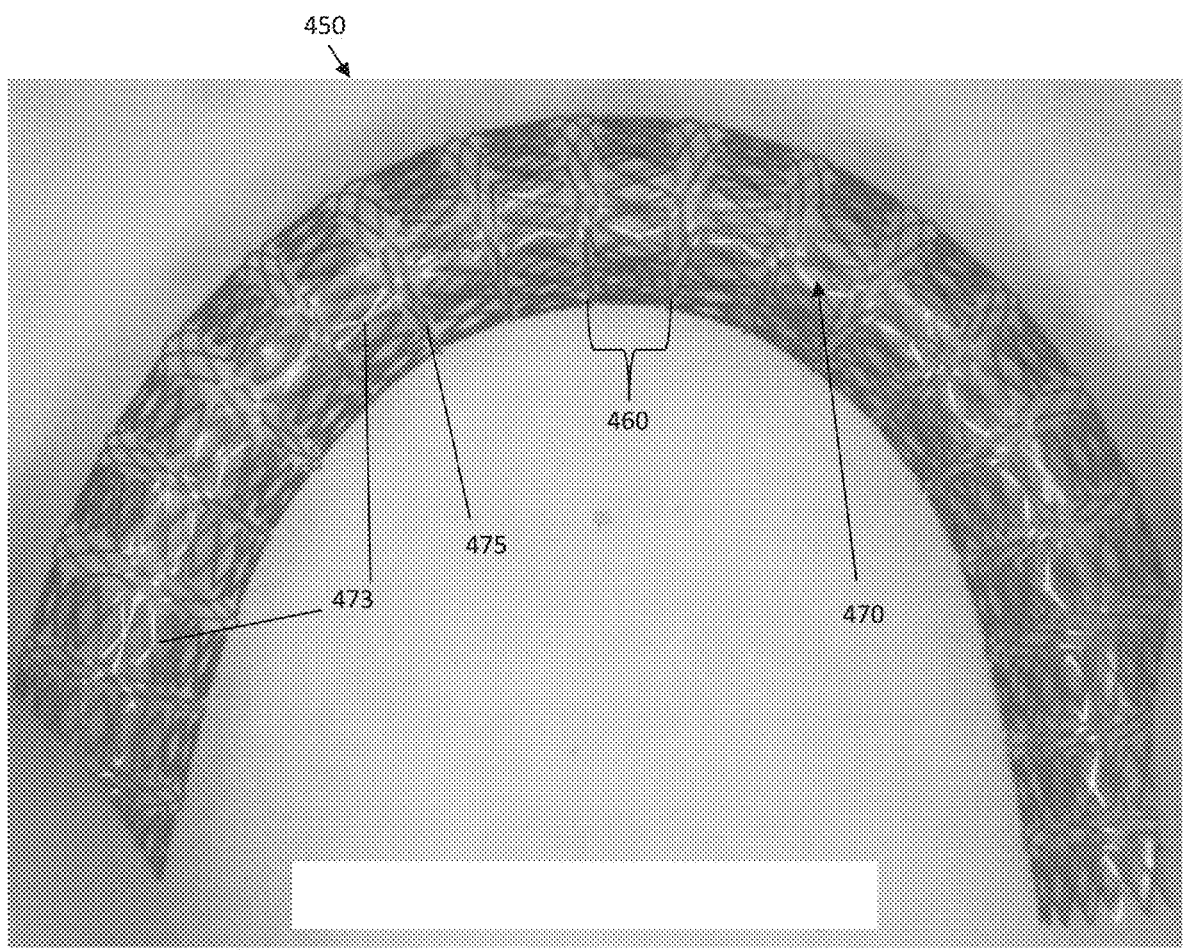
FIG. 8 is a low-density micro-stent shown in a 180-degree free bend.

FIG. 8 illustrates a low-density pattern stent 450 in a 180-degree free bend.

Figure 9A:
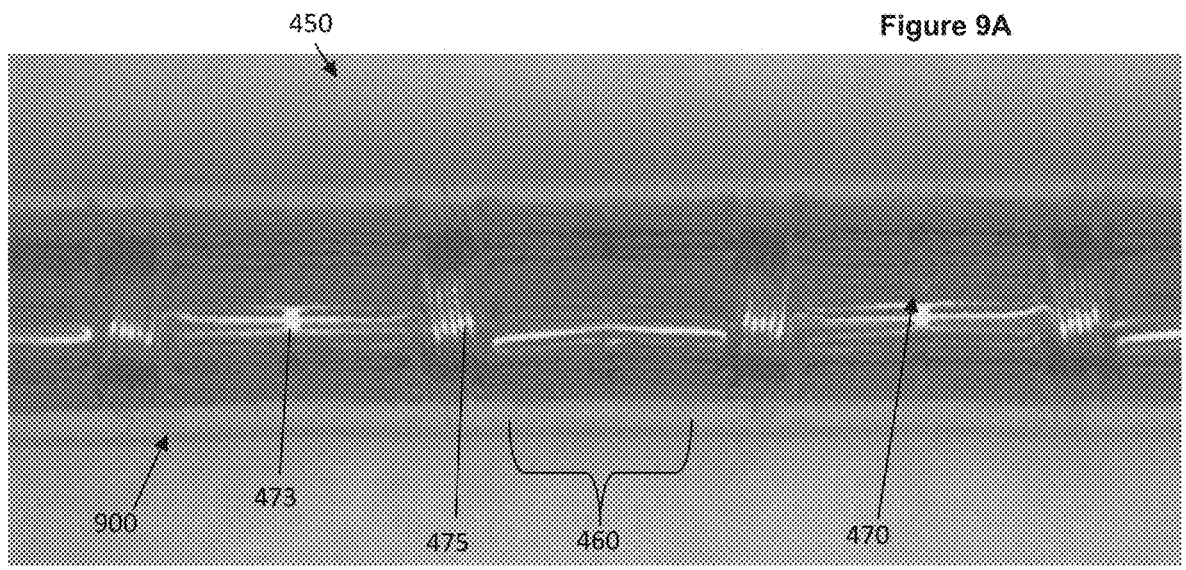
FIG. 9A is a low-density micro-stent crimped configuration constrained by a sub-millimeter inner diameter PTFE tube.
Figure 9B:
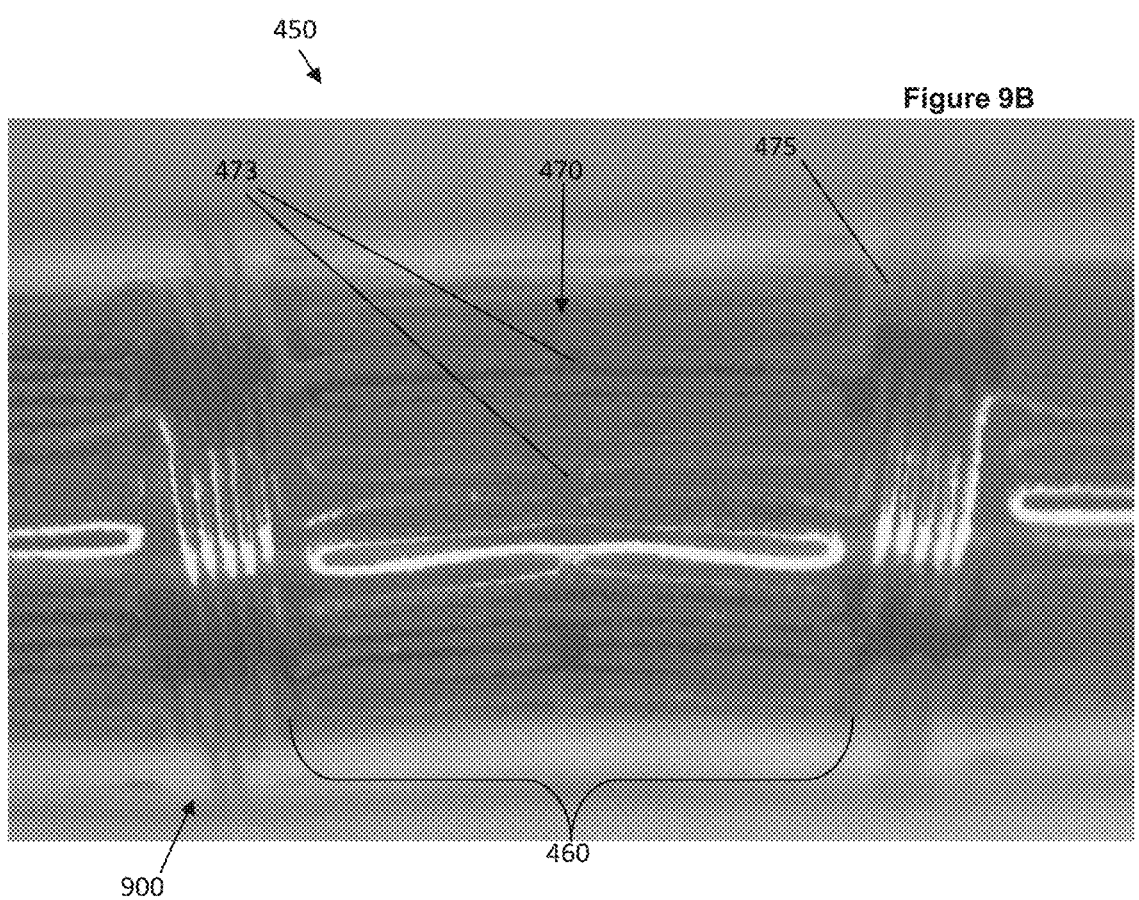
FIG. 9B is a zoomed in view of a section of the stent of FIG. 9A.

FIG. 9A illustrates a low-density pattern stent 450 in a crimped configuration constrained by a less than 1 mm inner diameter PTFE tube 900. FIG. 9B illustrates an enlarged view of a portion of the low-density pattern stent 450 of FIG. 9A.

As illustrated in FIGS. 4 and 7, in some embodiments, for the low-density hybrid pattern stent 450, the bridge members 475 are capable of expansion outward from the circumferential plane to serve as a distributed flare for device fixation to prevent migration in situ.

Some embodiments of the present invention may be fabricated by employing a vapor deposition technique which entails vapor depositing a stent-forming metal onto a substrate. The substrate may be planar or cylindrical and is either pre-patterned with one of the preferred geometries of first and interconnecting members, in either positive or negative image, or the substrate may be un-patterned. Where the substrate is un-patterned, the deposited stent-forming metal is subjected to post-deposition patterning to pattern the deposited stent-forming metal into one of the preferred geometries of the first and interconnecting members. In all embodiments of the present invention fabricated by vapor deposition techniques, the need for post-deposition processing of the patterned endoluminal stent, e.g., modifying the surface of the stent by mechanical, electrical, thermal or chemical machining or polishing, is eliminated or minimized.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of making an intravascular stent, comprising the steps of:
   a. vacuum depositing a metal hypotube onto a cylindrical substrate;
   b. patterning a stent pattern onto the deposited metal hypotube, wherein the pattern comprises a plurality of longitudinally extending struts defining a plurality of interconnected closed cells connected to each other along a first circumferential axis of the metal hypotube by interconnection points, and a plurality of elongate struts defining a plurality of bridge struts, each of the plurality of bridge struts extending along a second circumferential axis and having opposing ends that interconnect at the interconnection points between adjacent pairs of the plurality of interconnected closed cells at each opposing end of each of the plurality of bridge struts; and
   c. removing the stent pattern from the cylindrical substrate.

2. The method of claim 1, wherein the step of patterning further comprises patterning each of the plurality of bridge struts to be separated by at least two interconnected closed cells of the first plurality of interconnected closed cells along the first circumferential axis of the first plurality of interconnected closed cells.

3. The method of claim 2, wherein the step of vacuum depositing a metal hypotube onto a substrate further comprises the step of vacuum depositing a metal ribbon and winding the metal ribbon around a cylindrical substrate.

4. The method of claim 3, after the step of removing the stent pattern from the cylindrical substrate, further comprising the steps of:
   winding the ribbon around a mandrel;
   shaping the wound ribbon into a desired stent frame shape; and
   joining sections of the wound ribbon.

5. The method of claim 4, further comprising the step of patterning at least one surface of the thin ribbon, prior to or simultaneous with the step of winding around the mandrel.

6. The method of claim 4, wherein the step of patterning further comprises laser patterning to impart at least one feature on the at least one surface of the ribbon.

7. The method of claim 4, wherein the step of patterning further comprises forming a plurality of grooves on the at least one surface of the ribbon.

8. The method of claim 4, further comprising polishing the ribbon, prior to or simultaneous with the step of winding around the mandrel.

9. The method of claim 4, further comprising laser cutting a stent strut pattern into the thin ribbon, prior to, after, or simultaneous with the step of winding around the mandrel.

10. The method of claim 9, wherein the step of laser cutting is an athermal process characterized by low slag formation.

11. The method of claim 1, wherein the step of patterning comprises laser patterning to impart at least one feature on the at least one surface of the deposited metal.

12. The method of claim 11, wherein the laser patterning is an athermal process characterized by low slag formation during laser patterning.

13. The method of claim 1 wherein the metal hypotube is made of a material selected from the group consisting of of elemental titanium, vanadium, aluminum, nickel, tantalum, zirconium, chromium, silver, gold, silicon, magnesium, niobium, scandium, platinum, cobalt, palladium, manganese, molybdenum and alloys thereof.

14. The method of claim 1 wherein the step of patterning a stent onto the deposited metal hypotube and forming a first plurality of interconnected closed cells or forming a second plurality of interconnected closed cells further comprises forming each closed cell of the first plurality or second plurality of interconnected closed cells into a diamond expanded shape, circular expanded shape, elliptical expanded shape, triangular expanded shape, rectangular expanded shape, or square.

15. The method of claim 1, wherein the step of vacuum depositing further includes the step of providing a pre-patterned planar substrate and the step of patterning includes forming the pattern by vacuum depositing the thin film onto the pre-patterned planar substrate.

16. The method of claim 1, wherein the step of vacuum depositing metal onto a substrate further comprises the step of vacuum depositing a thin film metal having a thickness between 1 and about 1000 microns.

17. The method of claim 1, wherein the step of vacuum depositing metal onto a substrate further comprises the step of vacuum depositing layers of dissimilar metals.

18. The method of claim 1, further comprising the step of forming a plurality of grooves on a surface of the stent pattern.

19. The method of claim 1, further comprising removing oxide from the stent pattern.

20. The method of claim 1, further comprising electropolishing the stent pattern.

21. The method of claim 1, further comprising shape setting the stent pattern.

22. The method of claim 1, wherein the step of vacuum depositing a metal hypotube onto a cylindrical substrate further comprises the steps of vacuum depositing plural layers of metal to form laminated layers of metal.

23. The method of claim 1, wherein the first plurality of interconnected closed cells, the second plurality of interconnected closed cells, and the plurality of bridge members are configured in a pattern having blood flow diversion properties.

* * * * *